(12) United States Patent
Remon et al.

(10) Patent No.: US 6,436,630 B1
(45) Date of Patent: Aug. 20, 2002

(54) METHOD FOR TESTING THE TOXICITY OF CHEMICAL SUBSTANCES USING GASTROPODS

(75) Inventors: Jean Paul Remon, Melle; Els Adriaens, Aalter, both of (BE)

(73) Assignee: Universiteit Gent, Gent (BE)

( * ) Notice: Subject to any disclaimer, the term of this patent is extended or adjusted under 35 U.S.C. 154(b) by 0 days.

(21) Appl. No.: 09/763,930

(22) PCT Filed: Aug. 24, 1999

(86) PCT No.: PCT/EP99/06204

§ 371 (c)(1),
(2), (4) Date: Apr. 25, 2001

(87) PCT Pub. No.: WO00/13013

PCT Pub. Date: Mar. 9, 2000

(30) Foreign Application Priority Data

Aug. 26, 1998 (EP) .............................................. 98202851

(51) Int. Cl.$^7$ .................................................. C12Q 1/00
(52) U.S. Cl. ............................................ 435/4; 424/9.2
(58) Field of Search .............................. 435/4; 424/434, 424/493, 9.1, 9.2; 800/8, 9

(56) References Cited

U.S. PATENT DOCUMENTS 4,444,891 A    4/1984 Miwa et al. .................... 436/2

FOREIGN PATENT DOCUMENTS

DE          30 18 900         11/1980

OTHER PUBLICATIONS

Derwent WPI Database, Section PQ, week 8239, Nov. 23, 1981.

Bendetti, Effect of pollution on some freshwater species. I. . Histochemical and biochemical features of lead pollution of some organs of *Viviparus viviparus* L. (*Mollusca gstropoda*). Chemical Abstracts, vol. 97, No. 13, Sep. 27, 1982, p. 156.

Radwan Biochemical response of brown garden snails, *Helix aspersa* to chlorfluazuron and flufenoxuron. Chemical Abstracts, vol. 119, No. 9, Aug. 30, 1993, p. 406.

Marigomez, Tissue–level biomakers and biological effect of mercury on sentinel slugs, Arion ater. Chemical Abstracts, vol. 125, No. 11, Sep. 9, 1996, p. 430.

Anbarasu, Toxic effects of mercury (II) chloride on the field pest *Achatina fulica*. Chemical Abstracts, vol. 119, No. 11, Sep. 13, 1993, p. 328.

*Primary Examiner*—Ralph Gitomer
(74) *Attorney, Agent, or Firm*—Lee, Mann, Smith, McWilliam, Sweeney & Ohlson (57) ABSTRACT

An in vivo and an in vitro toxicity test method is described using an organisim or part of an organism from the class Gastropoda. The method is particularly useful for toxicity testing of chemical substances intended for application to human or animal mucosa, such as the intestinal, vaginal, buccal, nasal or respiratory mucosa. The test method may be used both as a screening test and also as a quantitative toxicity test suitable for ranking the toxicity of chemical substances.

23 Claims, 6 Drawing Sheets

METHOD FOR TESTING THE TOXICITY OF CHEMICAL SUBSTANCES USING GASTROPODS

The present invention relates to a method of testing the toxicity of a chemical substance in particular with reference to animal, especially human mucosal membranes, more especially single-layered mucosal surfaces such as human intestinal, nasal and respiratory mucosa and other mucosal surfaces such as vaginal and buccal mucosa.

TECHNICAL BACKGROUND

Higher animals, such as mice, rats, rabbits, dogs, cats, pigs, and monkeys, are usually used as test animals in conducting toxicity tests of substances. Breeding must be carried out under carefully controlled conditions over a long period of 2 to 2½ years. Thus, performing such toxicity tests is very time consuming and expensive. In the chemical and pharmaceutical industries, novel chemical substances are continually being synthesised to meet various industrial and health needs. Additionally, much research is being done to find new applications for known chemical substances. In each case, it is desirable to establish a rapid and inexpensive method for testing toxicity of these substances.

Toxicity testing using vertebrate animals to evaluate the safety of xenobiotics to humans has been severely criticised based on ethical and financial considerations. The principle alternative to in vivo animal testing is in vitro testing. Many factors such as nervous control, systemic blood flow, reduced motility and heterogeneous cell populations, however, are absent in simple cell culture models which reduces the value of in vitro testing. Bacteria, for instance, are prokaryotic organisms which are quite different from multicellular organisms which possess higher levels of biological organisation. There is therefore a tendency to use higher animals or parts of higher animals for testing of complex systems such as human mucosa.

In the workshop "The three Rs: The Way Forward" organised by the European Centre for the Validation of Alternative Methods (ECVAM) (Sheringham, Norfolk, UK, 30/5-3/6, 1995) some replacement alternative methods and approaches were proposed, for example, the use of "lower" organisms with limited sentience and/or not protected by legislation controlling animal experiments, including invertebrates, plants and micro-organisms. However, only nematodes, bacteria or insects were proposed as concrete alternatives to animal testing. The use of nematodes for toxicity testing is described in U.S. Pat. No. 4,444,891.

Investigations have demonstrated that the human mucosa, in particular the nasal mucosa allows effective drug absorption. Particularly for peptide drugs, nasal delivery is a promising alternative to parenteral administration. However, because of their high molecular size and hydrophilic properties at physiological pH values, peptides show poor transport characteristics across the hydrophobic membrane barriers. The absorption efficiency of intranasally administered peptides can be improved by the use of absorption enhancers, such as bile salts, laureth-9, fusidate derivatives or sodium taurodihydrofusidate (STDHF).

Such absorption enhancers play an essential role in nasal drug delivery. In particular, for peptides and proteins the use of absorption enhancers is often mandatory to reach an effective absorption from the nasal mucosa. Unfortunately, little is known about potential side effects of these substances, which is a drawback for the clinical application of absorption enhancers in nasal drug formulations. Looking more closely at the effects and the mechanisms underlying absorption enhancement of absorption enhancers on the nasal mucosa provides more information on their efficacy and safety. The mechanisms that lead to increased nasal drug absorption under the influence of enhancers are quite diverse and only partly understood. In some cases the solubility or the stability of the drug is increased, but absorption enhancers can also interact with the mucus layer, changing the mucus properties. Furthermore, the permeability of the nasal epithelium might also be increased due to interaction with the epithelial membranes.

When considering nasal drug delivery, the effects of drug and additives on nasal functions should be tested at an early stage. Because the self-cleaning capacity of the nose by the ciliary epithelium is vital for the removal of dust, allergens and bacteria from the nasal area of humans, it should not be influenced by nasal medication. Ciliary movement is a major factor for the mucociliary clearance in the upper airways. From patients with "immotile cilia syndrome" it is known that chronic nasal ciliary arrest leads to recurrent infections of the airways. Many drugs and additives inhibit nasal ciliary movement as demonstrated in vitro. For instance, lipophilic and mercuric preservatives, antihistamines, propranolol and dihydroxy bile salts are ciliostatic agents, all reducing the ciliary beat frequency within a short time. It is further important to investigate whether a ciliostatic effect is reversible after withdrawal of drug exposure. Nasal absorption enhancers should be devoid of any serious ciliotoxicity, and the feasibility of nasal drug administration may depend largely on the effects on the ciliated epithelial tissue.

The following methods for determining the cytotoxicity or mucociliary clearance time of chemical substances have been proposed: in situ tests on the rat nasal epithelium, in vitro determination of the influence of enhancers on the ciliary beat frequency of cilia of new-born chicken trachea and the use of the frog palate model in which the frog is decapitated, the upper palate is exposed and tested visually with the specific substance.

Not only nasal functions but also negative side effects should be determined at an early stage in drug or drug delivery development, ideally before clinical trials on humans. An example is the delivery of the β-blocker propranolol HCl via human buccal mucosa. This chemical caused severe ulceration of humans during clinical trials that took weeks to heal. It would be desirable to have a screening test method which could reliably screen out chemicals which cause such serious problems to humans.

Gastropods are molluscs and include snails and slugs. They generally have a single shell or none at all and often have an asymmetric body. A more extensive discussion of gastropods may be found in the Encyclopaedia Britannica. Until now gastropods, e.g. snails, have mainly be used in medical products and processes as described, for instance in U.S. Pat. Nos. 5,538,740, 4,473,640, 4,314,992, 3,889,006, 4,855,285, 3,885,012.

In the article by Marigomez et. al., Arch. Environ. Contam. Toxicol. 1996, 31(1), pages 54–62, the use of slugs as sentinel organisms ("Slug Watch") is described in soil quality assessment. The slugs may be used as a biomarker of exposure to metallic pollutants in the soil. Reference is only made to the reaction of slugs to mercury and there is no indication that the slugs may be used as a model for human mucosa.

It is an object of the present invention to provide a test method with which substances may be tested for their toxicity to animal and human membranes easily, rapidly, accurately and inexpensively.

An objective of the present invention is to provide a method for testing the toxicity of a substance using invertebrates in lieu of vertebrates.

Another objective of the present invention is to provide a test allowing easy replication of tests to improve the statistical interpretation of the results.

SUMMARY OF THE INVENTION

The present invention includes use of a gastropod for toxicity testing. The present invention includes a toxicity test method for modelling the irritation to vertebrate mucosal surfaces, in particular to human or other mammal mucosal surfaces, by a chemical substance comprising the steps of:

providing at least a part of the epithelium of the body or a part of the foot of a gastropod, a gastropod being an organism of the class gastropoda; and exposing the part of the epithelium or the part of the foot to the chemical substance to be tested.

In particular, the chemical substance may be brought into contact with the skin and/or the foot of the gastropod. The present invention includes both in vivo tests using the whole gastropod or in vitro tests on a part of a gastropod. The chemical substances are not limited to cosmetic or pharmaceutical chemical formulations but may be household or industrial items such as paints, lacquers, adhesives and solvents which may come into contact with the human or animal mucosal membranes.

According to this test the mucosal irritation can be easily and rapidly determined qualitatively, e.g. by visual observation of the colour or increase in the amount of mucus liberated from the foot of the gastropod. Mechanical vibration and other irritations may affect mucus production of gastropods. To avoid confusion with other effects it is preferred in accordance with the present invention if the gastropods are not subjected to other forms of stress or agitation during the tests except for the chemical substances to be tested. According to the toxicity test method of the present invention, mucosal damage can also be easily determined quantitatively by the release of mucus from the foot, by the loss of body weight of the gastropod, or by release of marker substances, proteins or enzymes from the foot. In particular, the toxicity of a substance can be determined quantitatively by measuring the amount of total protein and/or lactate dehydrogenase and/or alkaline phosphatase and/or cholesterol and/or phospholipids and/or other membrane components released from the foot mucosa of the gastropod after treatment with the chemical substance. An advantage of the test is that the mucus production caused by irritating substances can be simply measured. The method in accordance with the present invention provides a simple screening test for the toxicity of substances while also providing a model for single-layered mucosal surfaces such human intestinal, nasal and respiratory mucosa and other mucosal surfaces such as vaginal and buccal mucosa, which can allow accurate quantitative analysis. Hence, the test method of the present invention may provide both qualitative and quantitative test results, e.g. the release of proteins, enzymes or membrane components from the treated epithelium, and may be suitable as both a screening test and an accurate quantitative toxicity test.

The present invention will be described with reference to the following figures. The dependent claims define individually, separate embodiments of the present invention.

DESCRIPTION OF THE PREFERRED EMBODIMENTS

The present invention will be described with reference to certain embodiments but the invention is not limited to these but only by the claims. The present invention will mainly be described with reference to two species of gastropoda but the present invention is not limited to these species. The present invention will also mainly be described with reference to a certain classes of substances, e.g. drug absorption enhancers and local anaesthetics as might be used in dentistry, but the present invention is not limited to this type of substances. Further, due to the type and form of the chemical substances tested in he following examples of the invention, terrestrial slugs are preferred, i.e. those gastropoda which breathe via lungs (*gastropoda pulmonata*) as these slugs are easily kept and observed under laboratory conditions. However, the present invention is not limited to these types of substances nor to these types of gastropods For instance, other chemical substances may preferably be tested in liquid form, either in a solvent such as water or saline solutions in which case water snails or slugs, including sea slugs, may be the preferred test organism. The foot of the gastropod is of particular interest in accordance with the present invention as it provides a mucal surface which can be advantageously used for toxicity testing in accordance with the present invention and which can provide a suitable model of mucal membranes of higher animals, e.g. vertebrates, in particular humans and other mammals.

End points of the toxicity tests in accordance with the present invention may include one or more of: mucus production, change of mucus colour, loss in body weight and release of biochemical marker substances. Each or all of these end points may provide either a qualitative or a quantitative ranking of the degree of irritation. It should be understood that the term "toxicity" includes allergic reactions so that toxicity testing in accordance with the present invention also includes testing for allergic reactions to substances. Such reactions are common with mucal membranes.

In accordance with one embodiment of the present invention, a living gastropod such as a hermaphrodite terrestrial, air-breathing slug, Arion sp. may be used as a test organism. The body wall of such slugs consists of an outer single-layered epithelium composed of epithelial and mucus secreting cells overlying connective tissue. The foot of the slugs consists of different epithelial cell types with distinct functional roles. The lateral bands of the foot are composed of microvillous epithelial cells that resemble those of absorptive surfaces in other animal systems. The medial band is composed of ciliated cells and is specialised for locomotion. The skin of slugs is soft with no evidence of keratinisation or cuticle production. It has been found in accordance with this invention that the foot epithelia of slugs is a good model for absorptive epithelia of higher animals such as vertebrates and especially mammals including humans.

Initially, the slugs are kept on a culture under controlled conditions of temperature and humidity until they have reached a stable body weight. The purpose of achieving a stable body weight is to improve the reproducibility of the results, particularly as the release of substances from the slugs may conveniently be measured in terms of the body weight thereof. The slugs are then isolated from the culture and placed in a vented plastic box lined with moist paper towel and placed at 95% relative humidity at 20° C. seven days before the start of an experiment. The slugs were not bred in any particular way, i.e. they were wild slugs. It is anticipated that even more accurate and reproducible results can be obtained by selective breeding of the slugs, although as shown by the test results this is not a necessary requirement of the present invention to obtain accurate and useful data.

The test procedure is simple and rapid. The chemical substance to be tested is applied directly to the mucosal membrane of a slug, e.g. to the foot, by placing the slug individually in a petri dish containing the test substance. Slugs treated with phosphate buffered saline are used as a negative control. As a positive control slugs treated with a known toxic substance, benzalkonium chloride, were used.

Because the mucosal epithelium of interest is located at the outside of the slug the effect of substances can be easily observed. Irritating substances can cause an increased mucus production of the slugs which can be observed visually. This can also be simply measured by weighing the petri dish before and after the treatment of the slugs with the chemical substance (with the slugs removed in each case). Additionally an indirect response to epithelial damage caused by a chemical substance may be determined by the reduction of the body weight of the slugs due to the leakage of haemolymphatic fluids through the damaged foot surface.

After the treatment the slugs are transferred individually to a fresh petri dish containing phosphate buffered saline. After a suitable exposure time, e.g. 1 hour the phosphate buffered saline is collected and analysed for the presence of proteins and/or enzymes, e.g. lactate dehydrogenase and/or alkaline phosphatase, or other marker substances released from the foot or epithelium of the slug, for example membrane associated components such as phospholipids or cholesterol. This procedure can be repeated after periods of several hours in order to determine the reversibility of the cell damage caused by the test chemical substance. The concentration or amount of the chemical substance to be tested can be changed and the influence of the concentration can be easily examined. The exposure time can also be changed if required. The slugs can be treated during several successive days in order to investigate the subchronical effect of substances on the foot mucosa.

EXAMPLE 1

Seven days before the start of the experiment the slugs were isolated in a plastic box lined with moist paper towel and placed at 95% relative humidity at 20° C. As test substances didecanyol-L-α-phosphatidylcholine (DDPC) and sodium deoxycholate (SDC) were selected. Benzalkonium chloride (1% w/v), SDC (1% w/v) and DDPC (1%, w/v) were prepared in phosphate buffered saline (PBS, pH 7.4). The slugs were daily incubated during 15 min with the test solution during five days. After the incubation period the slugs were placed on 500 μL PBS in a petri dish. The PBS was sampled every hour and refreshed with 500 μL PBS for 6 h after the treatment. During the test the slugs are preferably kept in a generally calm and normal state and are not subjected to mechanical vibrations or mechanical or electrical disturbances which may affect mucus production.

The enzymes (lactate dehydrogenase (LDH) and alkaline phosphatase (ALP)) and total protein released into the PBS were determined. The slugs were weighed before and after the incubation period to determine the body weight changes. The mucus production was measured by weighing the petri dishes before and after the treatment with a test substance. The results are shown in Table 1 and shown graphically in FIGS. 1 to 5.

Figure 1:
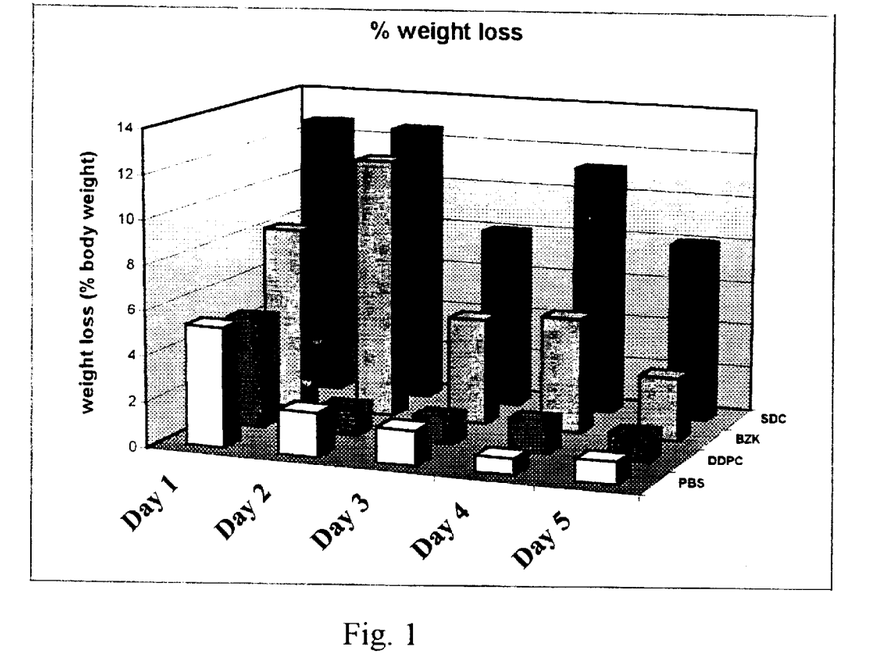
FIGS. 1 to 5 show the results (Table 1) of test example 1 in accordance with the first embodiment of the present invention.
Figure 2:
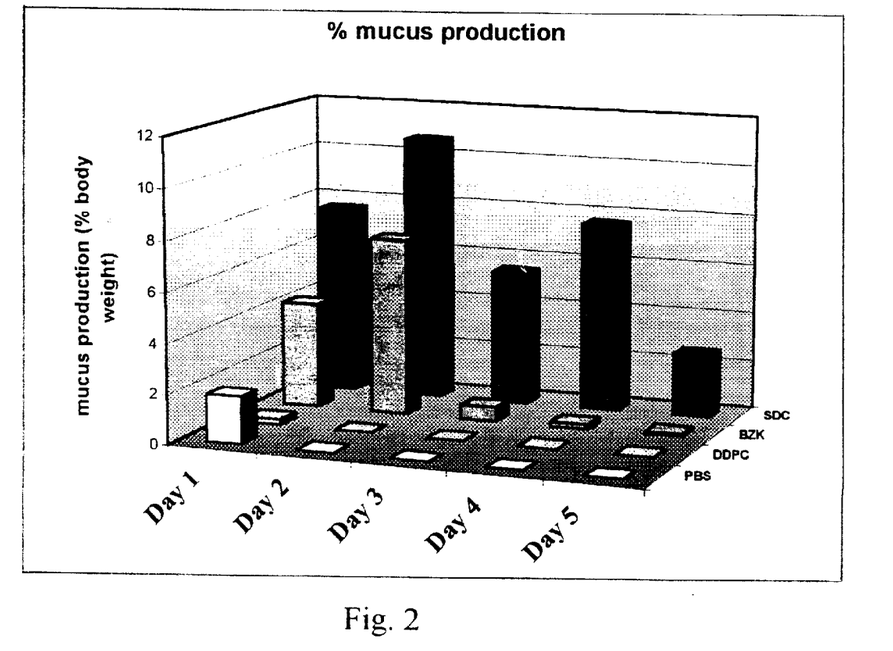
Figure 3:
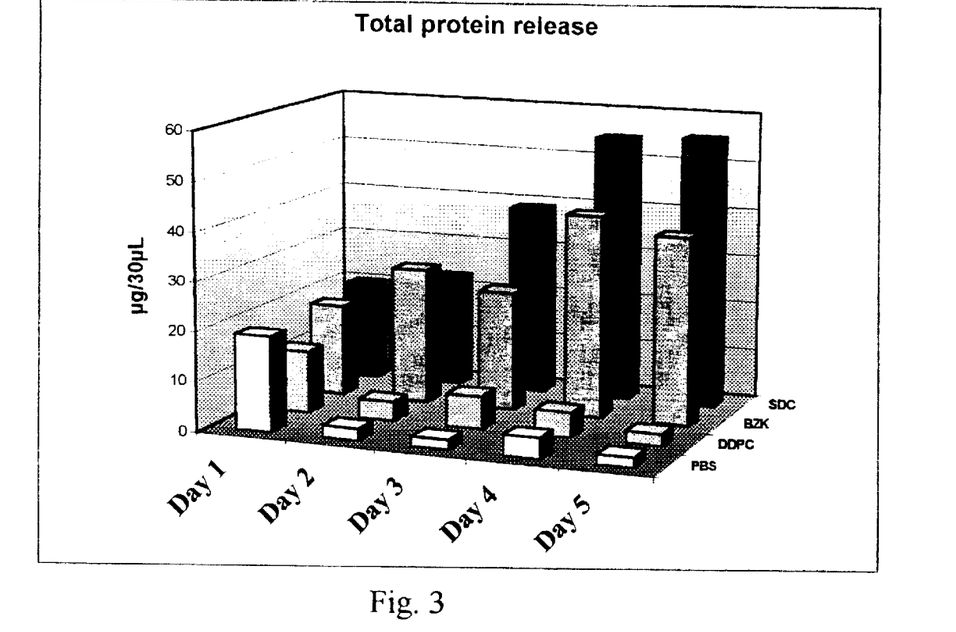
Figure 4:
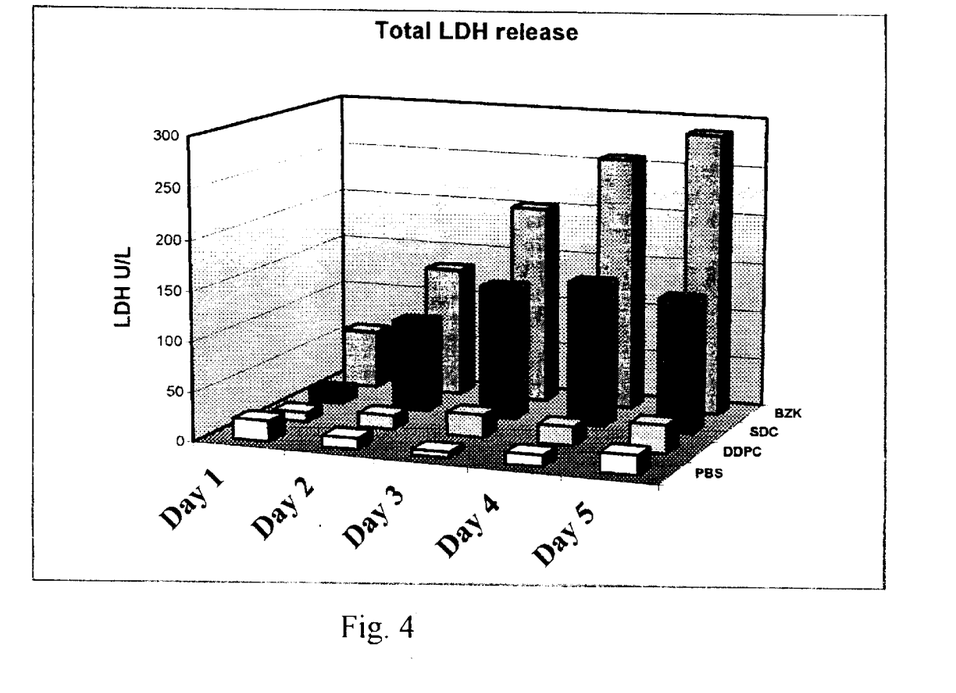
Figure 5:
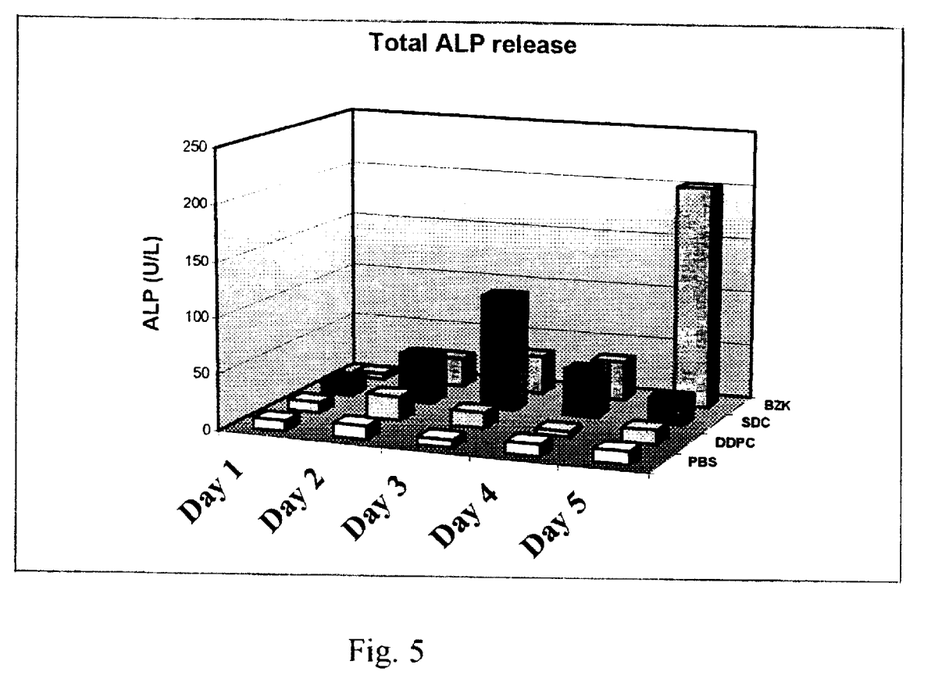
Figure 6:
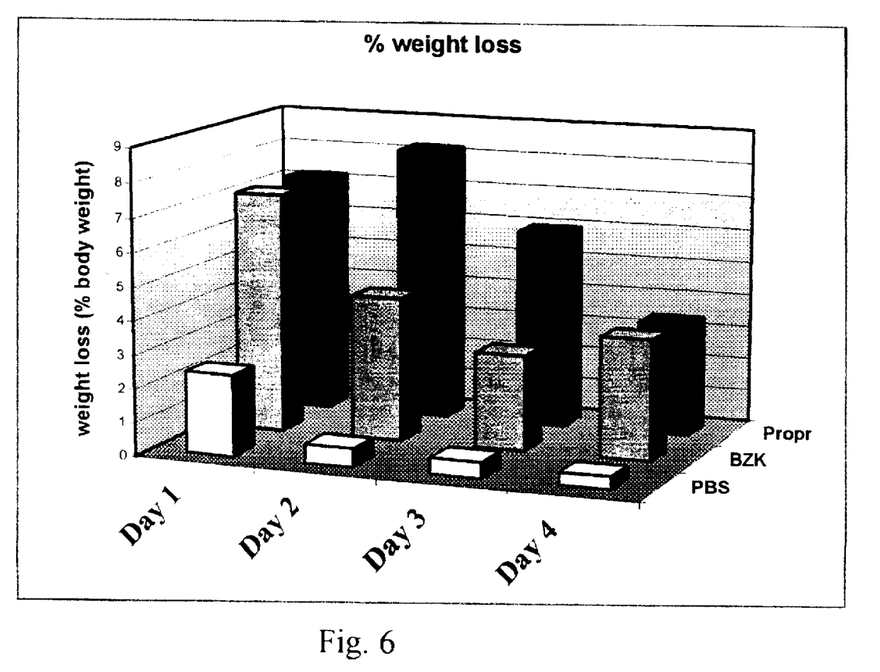
FIGS. 6 to 10 show the results (Table 2) of test example 2 in accordance with the first embodiment of the present invention.
Figure 7:
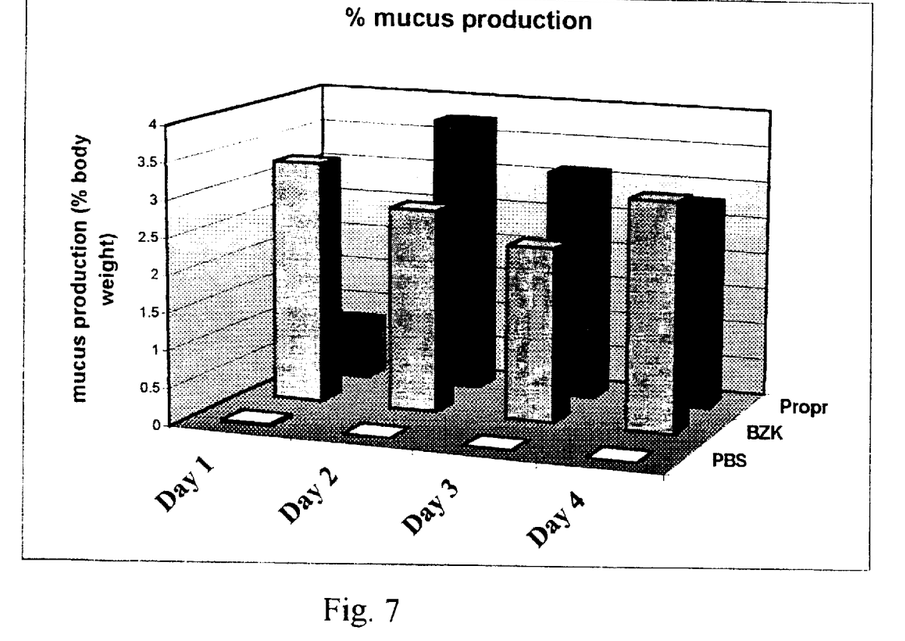
Figure 8:
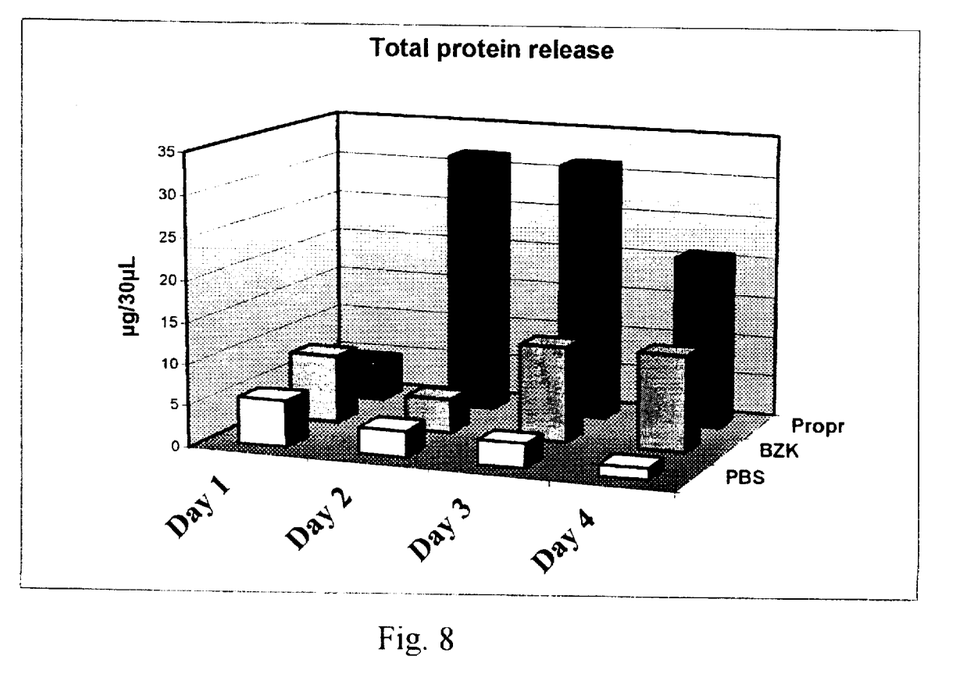
Figure 9:
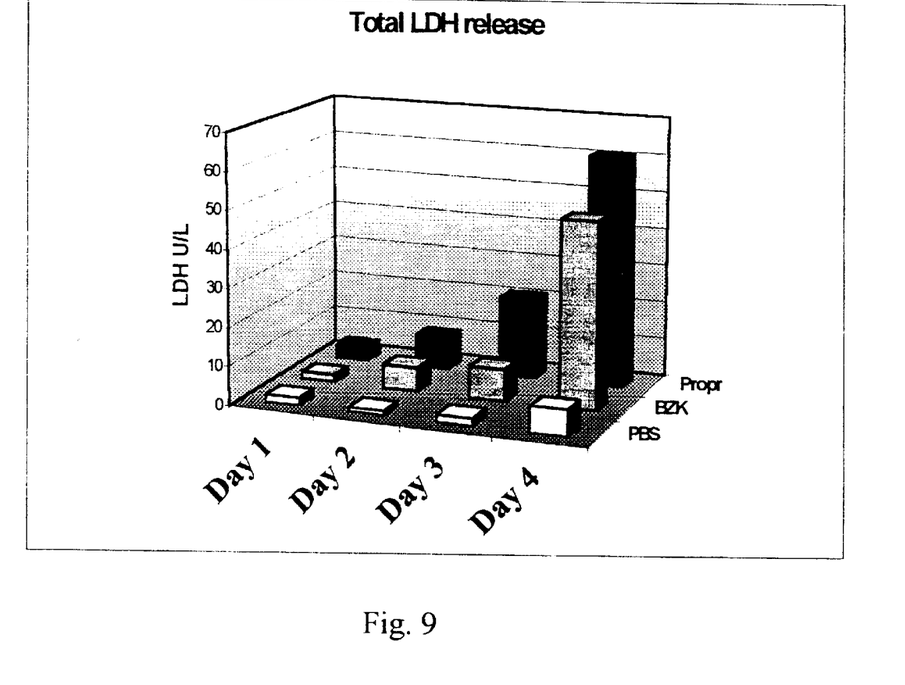
Figure 10:
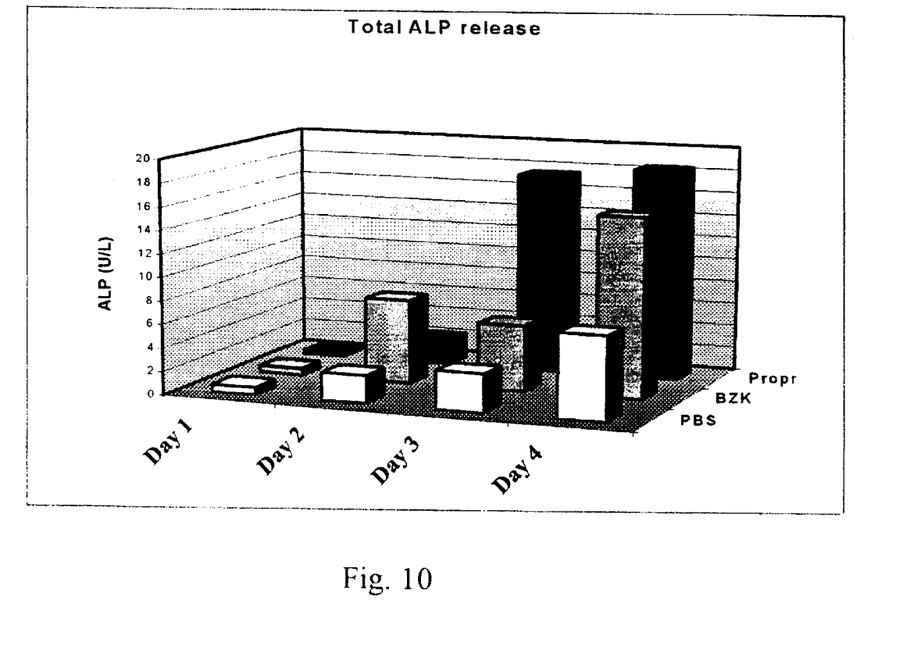

The results which are shown graphically in FIGS. 3 to 5. Total protein release and total LDH release climb steadily compared with the stable results for the control (PBS) and DDPC. There is also more ALP release than with the control or DDPC. These results provide clearly identifiable indicators that benzalkonium chloride or SDC cause severe membrane damage, whereas treatment with PBS or DDPC causes little or no damage. These results are not only in agreement with published data for these substances as determined by other methods but also the test method according to the present invention ranks the tested substances quantitatively in the same order as has been determined by other methods. Thus, the present invention may provide a test method which not only determines potential changes to the human mucosa when these changes are severe but may also provide an analytic tool which may be refined to assess more subtle sensitivities, including physicochemical factors such as the effects of aqueous to lipid partitioning in a drug, the pH, ionic strength or osmolarity of the drug solution, the charge and concentration of buffer species and even the dosage form. Due to the ease with which the test may be performed it is possible within an economically feasible time to carry out tests with many varied parameters once an initial screening has been used to narrow the selection. Of use in this respect are the quick and simple but rather less quantitative tests of weight loss and mucus production (FIGS. 1 and 2) which may also provide reliable toxicity information. This demonstrates that rapid screening tests can be carried out using these simpler analytic tests which have the advantage of not requiring complex test equipment, sophisticated chemical analysis or a long time to complete. Surprisingly, the use of wild slugs provides accurate results with a minimum of pre-test conditioning which means that a long breeding, nurturing and growth step can be avoided thus providing surprisingly rapid results.

TABLE I

Effect of PBS, Benzalkonium chloride (1% w/v), SDC (1% w/v) and DDPC (1% w/v) on the release of enzymes and total protein.

| Test substance | Day | % WL | % MP | Protein (μg/30 μL) | LDH (U/L) | ALP (U/L) | n |
|---|---|---|---|---|---|---|---|
| PBS | 1 | 5.25 | 1.9 | 18.98 | 20.61 | 8.9 | 3 |
|  | 2 | 1.91 | 0 | 2.36 | 11.35 | 11.91 | 3 |
|  | 3 | 1.53 | 0 | 1.92 | 5.43 | 7.02 | 3 |
|  | 4 | 0.72 | 0 | 4.07 | 11.18 | 10.42 | 3 |
|  | 5 | 0.98 | 0 | 2.04 | 19.51 | 11.47 | 3 |
| Benzalk | 1 | 8.25 | 4.3 | 18.50 | 59.47 | 5.01 | 3 |
|  | 2 | 11.73 | 7.15 | 27.60 | 132.95 | 26.17 | 3 |
|  | 3 | 4.72 | 0.56 | 24.12 | 202.53 | 34.46 | 3 |
|  | 4 | 5.09 | 0.2 | 41.46 | 257.91 | 35.62 | 3 |
|  | 5 | 2.78 | 0.1 | 38.24 | 287.93 | 202.7 | 2 |
| DDPC | 1 | 4.84 | 0.2 | 12.43 | 9.51 | 9.43 | 6 |
|  | 2 | 1.19 | 0 | 3.77 | 14.47 | 21.83 | 6 |

TABLE I-continued

Effect of PBS, Benzalkonium chloride (1% w/v), SDC (1% w/v) and DDPC (1% w/v) on the release of enzymes and total protein.

| Test substance | Day | % WL | % MP | Protein (μg/30 μL) | LDH (U/L) | ALP (U/L) | n |
|---|---|---|---|---|---|---|---|
| | 3 | 1.15 | 0 | 6.41 | 23.36 | 13.82 | 6 |
| | 4 | 1.39 | 0 | 4.98 | 19.07 | 4.55 | 6 |
| | 5 | 1.14 | 0 | 2.40 | 28.32 | 12.42 | 6 |
| SDC | 1 | 12.73 | 7.6 | 19.92 | 14.07 | 13.49 | 6 |
| | 2 | 12.60 | 10.7 | 22.84 | 93.01 | 43.02 | 6 |
| | 3 | 8.06 | 5.5 | 38.95 | 135.93 | 103.56 | 6 |
| | 4 | 11.28 | 7.6 | 54.76 | 146.89 | 42.22 | 3 |
| | 5 | 8.03 | 2.6 | 55.59 | 136.19 | 22.98 | 1 | where:
% WL represents reduction in weight (weight loss) caused by the 15 minute treatment expressed as % of initial body weight of the day, and
% MP represents mucus production expressed as % of the body weight at the start of the day before the treatment.
Data are expressed as total mean values (7 samples/day for each slug)

EXAMPLE 2

In example 2, slugs of species Arion were also isolated seven days before the start of the experiment and kept at 20° C. and 95% RH. As test substance a β-blocking agent propranolo HCl (1% w/v) was used. Benzalkonium chloride (1% w/v) and Propranolol (1% w/v) were prepared in PBS (pH 7.4). The slugs were daily incubated during 15 min with the test solution during four days. After the incubation period the slugs were placed on 500 μL PBS in a petri dish. The PBS was sampled every hour and refreshed with 500 μL PBS for 3 hours after the treatment.

The enzymes (LDH, ALP) and the total protein released into the PBS were determined. The change in body weight and the mucus production caused by the treatment were examined. The results are shown in Table 2 and shown graphically in FIGS. 6 to 10.

TABLE 2

Effect of PBS, Benzalkonium chloride (BZK) (1% w/v) and propanolol HCl (1% w/v) on the release of enzymes and total protein.

| Test substance | Day | % WL | % MP | Protein (μg/30 μL) | LDH (U/L) | ALP (U/L) | n |
|---|---|---|---|---|---|---|---|
| PBS | 1 | 2.42 | 0.03 | 5.61 | 1.87 | 0.62 | 8 |
| | 2 | 0.56 | 0 | 3.18 | 1.15 | 1.56 | 8 |
| | 3 | 0.49 | 0 | 2.97 | 1.87 | 3.23 | 8 |
| | 4 | 0.38 | 0 | 1.36 | 6.61 | 7.08 | 8 |
| BZK | 1 | 7.17 | 3.28 | 8.36 | 1.92 | 0.56 | 8 |
| | 2 | 4.32 | 2.75 | 4.08 | 6.27 | 3.42 | 8 |
| | 3 | 2.87 | 2.35 | 11.69 | 8.11 | 5.64 | 8 |
| | 4 | 3.61 | 3.09 | 11.79 | 48.65 | 15.59 | 8 |
| Propr | 1 | 7.17 | 0.77 | 4.89 | 3.43 | 0.35 | 8 |
| | 2 | 8.19 | 3.74 | 31.61 | 8.60 | 2.19 | 8 |
| | 3 | 5.95 | 3.11 | 31.36 | 20.98 | 17.50 | 8 |
| | 4 | 3.40 | 2.80 | 20.88 | 61.01 | 18.43 | 8 | where:
% WL represents the weight loss expressed as reduction in body weight caused by the 15 minutes of treatment, and
% MP represents mucus production expressed as % of the body weight at the start of the day before the treatment.
Data are expressed as total mean values (3 samples/day for each slug).

The test result indicate that 1% propranolol HCl causes considerable irritation. All indicators (FIGS. 6 to 10) showed high values with values indicating increased irritation compared to benzalkonium chloride. After 4 days of treatment with 1% propranolol HCl all the slugs were dead. These results show that 1% propranolol causes severe membrane damage. This is in agreement with published data which show that clinical testing on humans using propranolol HCl caused severe ulceration. The results confirm that the toxicity test in accordance with the present invention is capable of reliably screening out chemical substances which cause severe damage to human mucosa, thus providing medical practitioners with a useful tool to avoid clinical studies which cause harm to humans. The irritating potency of propranolol HCl is also shown by the reduction in body weight and the mucus production during the treatment. Although in this test the slugs were maintained in contact with the irritating substance until death, such an extreme case may be terminated more rapidly when this test method is used on a regular basis. The mucus excreted by the slugs was orange coloured whereas it is normally colourless. The production of orange mucus is therefore an indication of severe irritation and the test could normally be stopped within a short period of time when this is orange mucus is observed to avoid unnecessary discomfort to the slugs.

EXAMPLE 3

Slugs of species Arion and Limax were isolated seven days before the start of the experiment and kept at 20° C. and 95% RH. Slugs of the species Limax are terrestial slugs have lungs and also a small internal shell. As test substances hydroxypropyl-β-cyclodextrin (HPβCD), sodium tauro-24, 25-dihdrofiisidate (STDHF) and sodium deoxycholate were selected. Benzalkonium chloride (1% w/v), HPβCD (5% w/v), STDHF (1% w/v) and SDC (1% w/v) were prepared in phosphate buffered saline (PBS, pH 7.4). The slugs were daily incubated during 15 min with the test solution during five days. After the incubation period the slugs were placed on 500 μL PBS in a petri dish. The PBS was sampled every hour and refreshed with 500 μL PBS for 6 h after the treatment.

Figure 11:
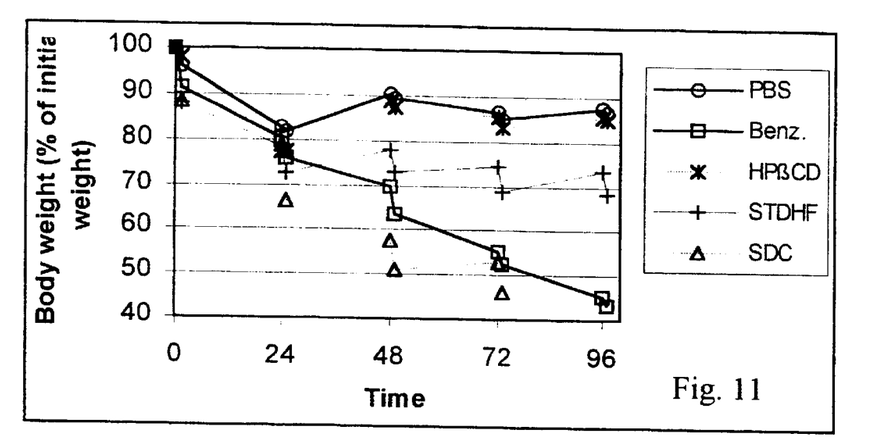
FIG. 11 shows reduction in body weight (% of initial body weight) caused by the different test substances for the slug species Arion (example 3, Table 3).
Figure 12:
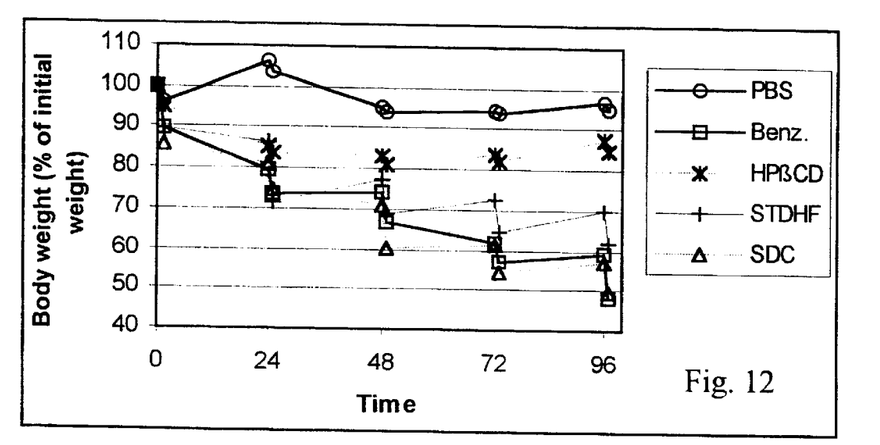
FIG. 12 shows reduction in body weight (% of initial body weight) caused by the different test substances for the slug species Limax (example 3, Table 4).

The enzymes lactate dehydrogenase (LDH) and alkaline phosphatase (ALP) and total protein released into the PBS were determined. The change in body weight and mucus production caused by the treatment were examined. The results are shown in Tables 3 and 4, the reduction in body weight caused by the treatment is shown in FIGS. 11 and 12.

Treatment with PBS and HPβCD causes no mucus production and low protein and enzyme release. STDHF caused an increased mucus production, a decrease in body weight and a slightly increased LDH release for both species. Benzalkonium chloride and SDC cause severe membrane damage, and a reduction in body weight to about 50% of the initial weight. The results of the species Arion treated with SDC are shown in Table 1 (Example 1).

For both species Arion and Limax the same ranking order of increasing toxicity could be obtained: PBS, 5% HPβCD<1% STDHF<1% SDC and 1% BAC. These results are in agreement with published data for these substances as determined by other methods.

TABLE 3

Effect of PBS, Benzalkonium chloride (1% w/v), HPβBCD (5% w/v) and STDHF (1% w/v) on the release of enzymes and total protein using the slug species Arion. Data are expressed as total mean values (7 samples/day for each slug).

| Test substance | Day | % MP | Protein (μg/30μL) | LDH (U/L) | ALP (U/L) | n |
|---|---|---|---|---|---|---|
| PBS | 1 | 0.83 | 17.26 | 13.87 | 6.92 | 3 |
| | 2 | 0 | 2.66 | 16.69 | 7.89 | 3 |

TABLE 3-continued

Effect of PBS, Benzalkonium chloride (1% w/v), HPβBCD (5% w/v) and STDHF (1% w/v) on the release of enzymes and total protein using the slug species Arion. Data are expressed as total mean values (7 samples/day for each slug).

| Test substance | Day | % MP | Protein (μg/30μL) | LDH (U/L) | ALP (U/L) | n |
|---|---|---|---|---|---|---|
|  | 3 | 0 | 2.38 | 14.69 | 2.69 | 3 |
|  | 4 | 0 | 1.18 | 11.28 | 14.09 | 3 |
|  | 5 | 0 | 1.53 | 1.16 | 3.34 | 3 |
| Benzalk. Chlor. | 1 | 4.24 | 14.16 | 20.69 | 20.76 | 3 |
|  | 2 | 1.37 | 8.65 | 90.39 | 16.32 | 3 |
|  | 3 | 2.77 | 19.55 | 150.71 | 15.24 | 3 |
|  | 4 | 0.5 | 23.14 | 121.73 | 31.68 | 3 |
|  | 5 | 0 | 33.22 | 145.05 | 16.09 | 3 |
| HPβCD | 1 | 0 | 17.54 | 20.62 | 6.8 | 6 |
|  | 2 | 0 | 2.93 | 11.47 | 16.14 | 6 |
|  | 3 | 0 | 4.33 | 17.25 | 4.74 | 6 |
|  | 4 | 0 | 3.14 | 10.09 | 9.7 | 6 |
|  | 5 | 0 | 5.05 | 0.49 | 4.3 | 6 |
| STDHF | 1 | 7.7 | 15.68 | 18.22 | 21.77 | 6 |
|  | 2 | 3.85 | 2.84 | 14.44 | 9.39 | 6 |
|  | 3 | 3.45 | 2.79 | 24.04 | 8.66 | 6 |
|  | 4 | 4.81 | 4.55 | 20.53 | 15.14 | 6 |
|  | 5 | 4.41 | 4.18 | 25.65 | 4.81 | 6 |

TABLE 4

Effect of PBS, Benzalkonium chloride (1% w/v), HPβCD (5% w/v), STDHF (1% w/v) and SDC (1% w/v) on the release of enzymes and total protein using the slug species Limax. Data are expressed as total mean values (7 samples/day for each slug).

| Test substance | Day | % MP | Protein (μg/30μL) | LDH (U/L) | ALP (U/L) | n |
|---|---|---|---|---|---|---|
| PBS | 1 | 1.24 | 0.09 | 0.62 | 2.58 | 3 |
|  | 2 | 0.03 | 8.94 | 3.44 | 4.68 | 3 |
|  | 3 | 0 | 4.86 | 1.35 | 6.46 | 3 |
|  | 4 | 0 | 5.11 | 7.52 | 1.14 | 3 |
|  | 5 | 0 | 5.57 | 1.76 | 2.27 | 3 |
| Benzalk. chlor. | 1 | 6.29 | 13.32 | 14.27 | 5.44 | 3 |
|  | 2 | 3.66 | 11.17 | 6.62 | 3.59 | 3 |
|  | 3 | 6.12 | 11.92 | 24.75 | 5.97 | 3 |
|  | 4 | 6.76 | 11.86 | 24.46 | 5.5 | 3 |
|  | 5 | 11.8 | 71.18 | 70.09 | 17.03 | 3 |
| HPβCD | 1 | 0 | 8.22 | 1.68 | 4.34 | 6 |
|  | 2 | 0 | 7.92 | 1.33 | 2.91 | 6 |
|  | 3 | 0 | 1.92 | 2.17 | 4.27 | 6 |
|  | 4 | 0 | 4.55 | 8.49 | 0.79 | 6 |
|  | 5 | 0 | 5.24 | 6.02 | 1.52 | 6 |
| STDHF | 1 | 6.85 | 14.48 | 1.65 | 3.81 | 6 |
|  | 2 | 6.16 | 11.67 | 4.29 | 6.49 | 6 |
|  | 3 | 7.52 | 6.27 | 6.02 | 5.09 | 6 |
|  | 4 | 6.75 | 10.4 | 18.23 | 3.28 | 6 |
|  | 5 | 6.6 | 10.36 | 10.63 | 3.62 | 6 |
| SDC | 1 | 11.16 | 10.1 | 9.01 | 11.62 | 6 |
|  | 2 | 10.27 | 15.78 | 13.6 | 3.34 | 6 |
|  | 3 | 13.01 | 18.04 | 26.15 | 2.62 | 5 |
|  | 4 | 19.38 | 35.04 | 85.8 | 6.24 | 5 |
|  | 5 | 8.11 | 88.14 | 145.71 | 28.79 | 4 | where: % MP = mucus production expressed as % of the body weight at the start of the day before the treatment.

EXAMPLE 4

The slugs of the species Arion were isolated seven days before the start of the experiment and kept at 20° C. and 95% RH. The following local anaesthetics were used as test substance: procaine HCl, lidocaine HCl, prilocaine HCl, tetracaine HCl and bupivacaine HCl. All test substances were prepared in PBS (pH 7.4) at 1% w/v concentrations. The slugs were daily incubate during 15 min with the test solution during five days. After the incubation period the slugs were placed on 1 ml PBS in a petri dish. The PBS was sampled every hour and refreshed with 1 ml PBS for 3 hours after the treatment.

Figure 13:
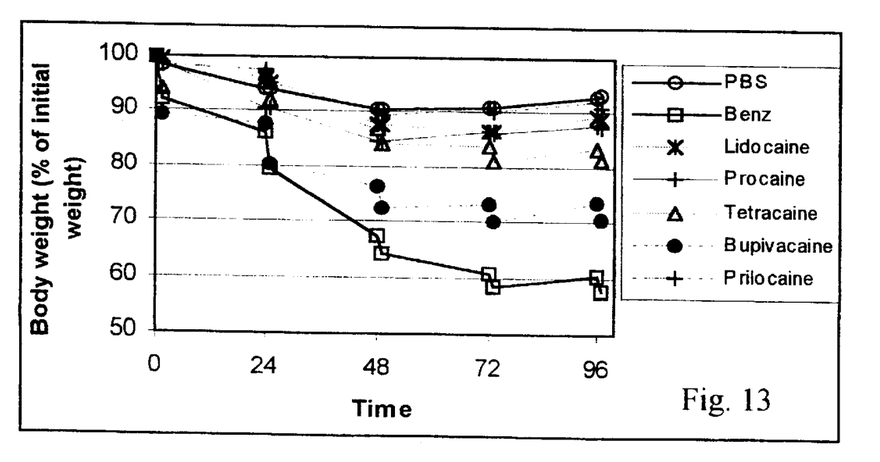
FIG. 13 shows reduction in body weight (% of initial body weight) caused by the different test substances (example 4, Table 5).

The total protein released into the PBS was determined. The change in body weight and the mucus production caused by the treatment were examined. The results are shown in Table 5 and FIG. 13. Treatment with PBS, procaine, lidocaine and lidocaine causes little or no damage. Tetracaine and bupivacaine resulted in an increased mucus production and an increased protein release. These results are in agreement with published data.

TABLE 5

Effect of PBS, benzalkonium chloride (1% w/v), procaine HCl (1% w/v), lidocaine HCl (1% w/v), prilocaine HCl (1% w/v), tetracaine HCl (1% w/v) and bupivacaine HCl (1% w/v) on the total protein release. Data are expressed as total mean values (3 samples/day for each slug)

| Test substance | day | % MP | Protein (μg/ml) | n |
|---|---|---|---|---|
| PBS | 1 | 0 | 140 | 25 |
|  | 2 | 0 | 69 | 25 |
|  | 3 | 0 | 69 | 25 |
|  | 4 | 0 | 61 | 25 |
|  | 5 | 0 | 76 | 25 |
| Benzalk. Chlor. | 1 | 4.77 | 596 | 25 |
|  | 2 | 4.22 | 873 | 25 |
|  | 3 | 1.32 | 988 | 24 |
|  | 4 | 0.35 | 1246 | 16 |
|  | 5 | 1.05 | 1258 | 10 |
| Procaine HCl | 1 | 0 | 204 | 10 |
|  | 2 | 0 | 62 | 10 |
|  | 3 | 0 | 92 | 10 |
|  | 4 | 0 | 54 | 10 |
|  | 5 | 0 | 70 | 10 |
| Lidocaine HCl | 1 | 0 | 119 | 10 |
|  | 2 | 0 | 70 | 10 |
|  | 3 | 0 | 119 | 10 |
|  | 4 | 0 | 75 | 10 |
|  | 5 | 0 | 89 | 10 |
| Prilocaine HCl | 1 | 0 | 139 | 10 |
|  | 2 | 0 | 62 | 10 |
|  | 3 | 0 | 72 | 10 |
|  | 4 | 0 | 65 | 10 |
|  | 5 | 0 | 82 | 10 |
| Tetracaine HCl | 1 | 3.45 | 413 | 10 |
|  | 2 | 2.48 | 130 | 10 |
|  | 3 | 1.15 | 120 | 10 |
|  | 4 | 1.29 | 128 | 10 |
|  | 5 | 0.65 | 149 | 10 |
| Bupivacaine HCl | 1 | 7.24 | 755 | 10 |
|  | 2 | 5.22 | 464 | 10 |
|  | 3 | 2.74 | 277 | 10 |
|  | 4 | 1.64 | 159 | 10 |
|  | 5 | 1.34 | 313 | 10 | where:
% MP = mucus production expressed as % of the body weight at the start of the day before the treatment.

The above tests described with reference to examples 1 to 4 are not an exhaustive list of tests in accordance with the present invention. Other tests are included within the scope of the present invention. For example, the cilia beat frequency and the onset of immotility of the cilia as well as the reversibility of the immotility can be observed visually on the foot of the gastropod and may be included as tests within the scope of the present invention and the attached claims.

The present invention is also not limited to in vivo testing but includes the use of at least part of a gastropod for in vitro testing. To perform an in vitro test the viscera of the gastropod are removed leaving a sack of muscle and epithelium. These may be kept viable in physiological saline solution during the conduction of the tests in which a chemical substance is applied to the foot and/or other epithelial parts of the gastropod. However, one advantage of using live gastropods is that the tests may be carried out over several days and allow quantitative measurement of the gastropod mucal excretions, whereas the in vitro test is best for quicker tests, e.g. cilia beat frequency or immotility. One advantage of the in vitro toxicity test in accordance with the present invention is that a wider range of gastropod species may be used conveniently whereas live animals may sometimes be more difficult to use in a test environment.

The tests and the results described above show that the methods in accordance with the present invention may provide a model of a mucous membrane of vertebrate animals, for example humans and other mammals, including human intestinal, vaginal, buccal, nasal and respiratory mucosa, from which qualitative and quantitative data on the toxicity of chemical substances with reference to these human or other animal mucal membranes may be obtained accurately, quickly and economically. A particular advantage of the test method according to the present invention is that the same basic test method and test equipment may be used both for rapid screening tests and more accurate quantitative tests.

What is claimed is:

1. A toxicity test method for modelling imitation to a vertebrate animal mucosal surface caused by a chemical substance, comprising the steps of:
   providing at least a part of the epithelium of the body or at least a part of the foot of a gastropod, a gastropod being an organism of the class gastropoda;
   exposing the at least part of the epithelium or the at least part of the foot of the gastropod to the chemical substance,
   performing at least one of qualitative and quantitative analysis of a reaction of the gastropod to the step of exposing, and
   correlating the reaction with the irritation.

2. The method according to claim 1, further comprising the step of bringing the gastropod to a stable weight before the step of exposing.

3. The method according to claim 1, wherein the step of qualitative analysis includes observing colour of the mucus released from the gastropod.

4. The method according to claim 2, wherein the step of quantitative analysis includes one of measuring the weight of the gastropod before and after the exposure step, measuring the weight of mucus released from the foot of the gastropod during and after the exposing step, measuring the amount of a protein released from the foot of the gastropod during and after the exposing step, and measuring the amount of an enzyme or membrane associated components released from the foot of the gastropod during and/or after the step of exposing.

5. The method according to claim 4, wherein the enzyme is one of alkaline phosphatase and lactate dehydrogenase.

6. The method according to claim 4, wherein the protein is the total protein released from the foot of the gastropod during and after the exposing step.

7. The method of claim 4, wherein the membrane associated components are phospholipids or cholesterol.

8. The method according to claim 1, wherein the gastropod is a pulmonary gastropod.

9. The method according to claim 8, wherein the gastropod is a terrestrial slug.

10. The method according to claim 9, wherein the slug is of the species Arion or Limax.

11. The method according to claim 1, wherein the providing step includes removing at least the viscera from the gastropod and maintaining the physiological viability of the remaining epithelium and/or foot.

12. The method according to claim 1, wherein the chemical substance is a cosmetic or a pharmaceutical formulation.

13. A test procedure comprising the steps of:
   carrying out on a first and a second chemical substance a toxicity test method suitable for modelling the irritation to a vertebrate animal mucosal surface, the toxicity test method comprising the steps of:
      providing at least a part of the epithelium of the body or at least a part of the foot of a gastropod, a gastropod being an organism of the class gastropoda;
      exposing the at least part of the epithelium or the at least part of the foot of the gastropod to the first and second chemical substance to be tested, and
   performing at least one of qualitative and quantitative analysis of a reaction of the gastropod to the step of exposing;
   correlating the reaction with the irritation; and
   ranking the first and second chemical substances.

14. The test procedure according to claim 13, wherein the toxicity test method further comprises the step of bringing the gastropod to a stable weight before the step of exposing.

15. The test procedure according to claim 13, wherein the step of qualitative analysis includes observing the colour of the mucus released from the gastropod.

16. The test procedure according to claim 13, wherein the step of quantitative analysis includes one of measuring the weight of the gastropod before and after the exposure step, measuring the weight of mucus released from the foot of the gastropod during and after the exposing step, measuring the amount of a protein released from the foot of the gastropod during and after the exposing step, and measuring the amount of an enzyme or membrane associated components released from the foot of the gastropod during and/or after the step of exposing.

17. The test procedure according to claim 16, wherein the enzyme is one of alkaline phosphatase and lactate dehydrogenase.

18. The test procedure according to claim 16, wherein the protein is the total protein released from the foot of the gastropod during and after the exposing step.

19. The test procedure according to claim 16, wherein the enzyme or membrane associated components are phospholipids or cholesterol.

20. The test procedure according to claim 13, wherein the gastropod is a pulmonary gastropod.

21. The test procedure according to claim 20, wherein the gastropod is a terrestrial slug.

22. The test procedure according to claim 21, wherein the slug is of the species Arion or Limax.

23. The test procedure according to claim 13, wherein in the toxicity test method the providing step includes removing at least the viscera from the gastropod and maintaining the physiological viability of the remaining epithelium and/or foot.

* * * * *